(12) United States Patent
Hurwitz

(10) Patent No.: US 8,703,174 B2
(45) Date of Patent: *Apr. 22, 2014

(54) JOINT PRESERVING NUTRITIONAL VITAMIN, MINERAL AND HERBAL PET SUPPLEMENT

(75) Inventor: Marni Markell Hurwitz, Far Hills, NJ (US)

(73) Assignee: I did It Inc, Far Hills, NJ (US)

( * ) Notice: Subject to any disclaimer, the term of this patent is extended or adjusted under 35 U.S.C. 154(b) by 1664 days.

This patent is subject to a terminal disclaimer.

(21) Appl. No.: 11/521,900

(22) Filed: Sep. 15, 2006

(65) Prior Publication Data

US 2008/0069862 A1    Mar. 20, 2008

(51) Int. Cl.
| | |
|---|---|
| A61K 38/39 | (2006.01) |
| A61K 31/7008 | (2006.01) |
| A61K 31/59 | (2006.01) |
| A61K 31/122 | (2006.01) |
| A61K 31/375 | (2006.01) |
| A23K 1/00 | (2006.01) |
| A61K 33/10 | (2006.01) |
| A61K 33/06 | (2006.01) |
| A61K 33/22 | (2006.01) |
| A61K 33/30 | (2006.01) |
| A61K 33/32 | (2006.01) |
| A61K 33/34 | (2006.01) |

(52) U.S. Cl.
USPC .......... 424/442; 424/630; 424/639; 424/641; 424/657; 424/682; 424/686; 424/687; 514/17.2; 514/62; 514/167; 514/168; 514/474; 514/682; 514/801; 514/904

(58) Field of Classification Search
None
See application file for complete search history.

(56) References Cited

U.S. PATENT DOCUMENTS

| | | | |
|---|---|---|---|
| 4,804,745 A | 2/1989 | Koepff et al. | 530/356 |
| 5,162,506 A | 11/1992 | Hadden | 530/412 |
| 5,364,845 A | 11/1994 | Henderson | 514/54 |
| 5,399,347 A | 3/1995 | Trentham et al. | 424/184.1 |
| 5,587,363 A | 12/1996 | Henderson | 514/54 |
| 5,645,851 A * | 7/1997 | Moore | 424/439 |
| 5,888,514 A * | 3/1999 | Weisman | 424/94.1 |
| 6,156,355 A | 12/2000 | Shields, Jr. et al. | 426/74 |
| 6,238,672 B1 * | 5/2001 | Chen | 424/728 |
| 6,428,817 B1 | 8/2002 | Collin | 424/725 |
| 6,447,809 B1 * | 9/2002 | Krumhar et al. | 424/602 |
| 6,524,609 B1 | 2/2003 | Myers | 424/439 |
| 6,596,303 B1 | 7/2003 | Bui et al. | 424/442 |
| 6,596,313 B2 * | 7/2003 | Rosenbloom | 424/464 |
| 6,780,841 B2 | 8/2004 | Ishaq | 514/2 |
| 6,974,841 B1 | 12/2005 | Rapisarda | 514/783 |
| 2004/0234579 A1 * | 11/2004 | Finke | 424/442 |
| 2005/0100622 A1 * | 5/2005 | Nair et al. | 424/777 |

* cited by examiner

*Primary Examiner* — Ernst Arnold
(74) *Attorney, Agent, or Firm* — Ernest D. Buff; Ernest D. Buff & Assoc. LLC

(57) ABSTRACT

A pet supplement includes a joint preserving and joint rebuilding composition comprising chicken collagen type II, glucosamine hydrochloride and chondroitin sulfate, a vitamin composition comprising vitamins C, D and K, a mineral composition comprising calcium, magnesium, zinc, copper, manganese and boron, a herbal anti-oxidant cofactor blend comprising citrus bioflavonoids, red grapes anthocyanins, turmeric rhizome, *boswellia* resin and fennel seed. Each of these ingredients is intimately mixed into the pet supplement and orally delivered to the pet in the form of a segment, paste or powder having a size and weight or other dosage measuring feature adjusted in accordance with the pet's weight. A synergistic action between these ingredients preserves and rebuilds the pet's joints, and is nutritionally beneficial for the pet.

23 Claims, No Drawings

JOINT PRESERVING NUTRITIONAL VITAMIN, MINERAL AND HERBAL PET SUPPLEMENT

BACKGROUND OF THE INVENTION

1. Field of the Invention

The present invention relates to a pet nutritional supplements; and more particularly, to a nutritional supplement composition having synergistically active vitamins, minerals and anti-inflammatory herbal constituents especially suited to rebuild and preserve joint functionality and improve the overall health of a pet.

2. Description of the Prior Art

Pet and human supplements are known in the art. They comprise vitamins and minerals, various herbal products and, more recently, products that are designed to improve joint health and relieve arthritis pain. The arthritis relieving compositions are mostly anti-inflammatory pain relief compounds such as aspirin, acetaminophen, ibuprofen or naproxen. Compositions containing glucosamine are known to be beneficial to both humans and pets that sufferer from osteoarthritis pain. Since glucosamine is a precursor for glycosaminoglycans, and glycosaminoglycans are a major component of joint cartilage, supplemental glucosamine may help to rebuild cartilage and treat arthritis. Commonly sold forms of glucosamine are glucosamine sulfate and glucosamine hydrochloride. Glucosamine is often sold in combination with other supplements such as chondroitin sulfate and methylsulfonylmethane. Generally vitamin C is needed together with glucosamine sulfate. Chondroitin sulfate is a sulfated glycosaminoglycan (GAG) composed of a chain of alternating sugars (N-acetyl-galactosamine and glucuronic acid). It is usually found attached to proteins as part of a proteoglycan. Chondroitin sulfate is a major structural component of cartilage and provides much of its resistance to compression. Most of these supplements derive the Chondroitin Sulfate from bovine cartilage or velvet deer antler or shark cartilage. Methylsulfonylmethane (MSM, or dimethylsulfone) is an organic sulfur compound belonging to a class of chemicals known as sulfones. It occurs naturally in some primitive plants and is present in small amounts in many foods and beverages. MSM is also known as dimethylsulfone, or DMSO2, a name that reflects its close chemical relationship to dimethyl sulfoxide (DMSO), which differs only in the oxidation state of the sulfur atom. MSM is the primary metabolite of DMSO in humans, and it shares some of the properties of DMSO. Collagen of type from chicken and other sources have been used as supplements. Cross linking of collagen molecules to form strong cartilages requires copper. None of the prior art disclosures combines collagen with glucosamine compounds, Chondroitin sulfate, and vitamins and minerals to provide a pet supplement composition that works synergistically to preserve and rebuild joint tissue.

Studies have shown that collagen is a complex structural protein, which provides strength and flexibility to skin, hair and nails. Collagen is an essential and major component of muscles, tendons, cartilage, ligaments, joints and blood vessels in the human or pet body. There are three main types of collagen: I, II and III. Types I and III are primarily found in skin, tendon and bone. In contrast, type II is found predominantly in articular cartilage. Collagen is an unusual protein, in that the, proportion of glycine residues is nearly one-third, which is unusually high in comparison to other typical proteins. Proline is also present to a much greater extent in collagen than in most other proteins. Moreover, collagen contains two amino acids, 4-hydroxyproline and 5-hydroxylysine, that are found in very few other proteins. The amino acid sequence of collagen is remarkably regular, nearly every third amino acid being glycine. In addition, the sequence glycine-proline-hydroxyproline recurs frequently. In contrast, globular proteins rarely exhibit regularities in their amino acid sequences (Stryer, L., Biochemistry, Third Edition, W. H. Freeman and Co., New York, 1988, pp. 262). In 1986, collagen was sold for the first time in the United States for use as a food supplement. Collagen (a mixture of Types I and III) was extracted from calf skin tissue, hydrolyzed and prepared in powdered form for use as a dietary supplement. The composition was sold under the name "Hydrolyzed Collagen Beauty Supplement™" (Smarter Nails & Hair, Inc., Newport Beach, Calif.). In 1987, "Hydrolyzed Collagen Beauty Supplement Tablet™" (Smarter Nails & Hair, Inc., Newport Beach, Calif.) was sold. This product comprised collagen powder and 10 mg vitamin C compressed into 1,000 mg tablets. Several patents are related to producing collagen fibers from animal tissues and hydrolyzing the collagen. At least one other patent discloses hydrolyzing collagen to a smaller protein chain length for superior biological absorption.

U.S. Pat. No. 4,804,745 to Koepff et al. discloses agents for the treatment of arthroses. These agents contain collagen peptides produced by enzymatic hydrolysis for the treatment of degenerative joint diseases. These peptides can be obtained from animal skin, animal bones and other sufficiently purified connective tissue and have average molecular weights of between 10,000 and 80,000.

U.S. Pat. No. 5,162,506 to Hadden discloses a process for preparing collagen fibers from tissue. This process produces collagen fibers by comminuting collagen containing tissues, drying the comminuted product and milling the dried material while maintaining the temperature sufficiently low to prevent substantial conversion of collagen to gelatin. The collagen fiber product is particularly useful for restructuring poorly textured meats, mechanically recovered meat products, offal, fish, fish products and other protein products to improve textural properties, water retention, fat retention, eating quality, juicines, succulence, shape, size retention and protein content. The collagen fibers are not of the type that rebuilds joints and are not a pet supplement. Moreover, the product does not contain needed vitamins.

U.S. Pat. No. 5,364,845 to Henderson discloses a glucosamine, chondroitin and manganese composition for the protection and repair of connective tissue. This therapeutic composition and method is for the protection, treatment and repair of connective tissue in mammals. This composition comprises glucosamine hydrochloride, chondroitin sulfate and manganese ascorbate, which catalyzes the production of collagen and proteoglycans from the glucosamine and the chondroitin sulfate. The composition does not contain chicken collagen type II. In addition, the composition does not provide all the vitamins and mineral supplements. There are no herbal anti-oxidants present in the composition.

U.S. Pat. No. 5,399,347 to Trentham et al. and Trentham et al. discloses a method of treating rheumatoid arthritis with type II collagen. This method uses a pharmaceutical formulation for the treatment of autoimmune arthritis and animal models therefore in mammals, including humans, by the oral, enteral or by-inhalation administration of whole collagen protein or biologically active peptide fragments of collagen. The type II collagen in amounts of 0.1 to about 1 mg/day is dissolved in a physiologically acceptable aqueous acidic medium. This work is also published as an article [Science 261:1727-1729, 1993] entitled "The Effective Treatment Of Rheumatoid Arthritis (Ra) With Water-Soluble Whole Chick Collagen Type Ii Or Biologically Active Peptides Derived Therefrom". The mechanism by which the effect is believed to occur is via oral tolerization to autoantigens. The type II collagen in acidic medium does not contain vitamins and minerals and herbal anti-oxidants. The composition is not specifically intended for pet usage.

U.S. Pat. No. 5,587,363 to Henderson discloses aminosugar and glycosaminoglycan composition for the treatment and repair of connective tissue. This therapeutic composition is for the protection, treatment and repair of connective tissue in humans and animals. The method for the treatment of connective tissue in humans and animals is by the administration of the composition. The aminosugar is selected from the group consisting of glucosamine, glucosamine salts and mixtures in combination with a glycosaminoglycan selected from the group consisting of chondroitin, chondroitin salts. The dose of glycosaminoglycan for humans and small animals ranges from 50 mg to 200 mg while large dogs need 250 mg to 1000 mg.

U.S. Pat. No. 6,156,355 to Shields, Jr., et al discloses breed-specific canine food formulations. This breed-specific dog food formulation comprises chicken meat as the major ingredient, rice as the predominant (or sole) grain source, fruit and/or vegetable fiber as the primary or sole fiber source, unique fat and antioxidant blend, vitamins, herbs and spices, carotenoids, with no corn or artificial colors, preservatives, flavors or sugars. The formulation also comprises fatty acids, yucca extract to control joint inflammation, manganese supplementation (cofactor in enzymes in chondroitin synthesis), zinc supplementation (protein and DNA synthesis), iron and vitamin C (for the hydroxylation of proline during collagen formation) and copper (for cross-linking of collagen molecules to provide cartilage strength) as well as biotin and choline (for proteoglycan formation and aggregation). The ingredients listed above are added in the diets specifically designed for breed groups with a high propensity of bone and joint problems, including herding dogs. The formulation does not contain all the vitamins and minerals needed and does not contain glucosamine component, chondroitin sulfate and collagen.

U.S. Pat. No. 6,428,817 to Collin discloses Companion animal therapeutic treat. This palatable dosage is in the form of a "jerky stick" or treat for companion animals which includes sea cucumber fractions alone or in combination with glucosamine sulfate and/or glucosamine hydrochloride, and/ or sea vegetables, and/or green tea. Such jerky stick contains an effective amount of sea cucumber material for the inhibition or modulation of arthritic or nutritional problems in dogs, cats, and also contains palatability co-factors, which render the jerky stick attractive to the animal in need. This jerky treat does not have any vitamins or collagen.

U.S. Pat. No. 6,524,609 to Myers discloses treating arthritis in animals with dietary supplements. This biscuit form of dietary supplement for dogs is for treating arthritis and joint discomfort and comprises cereal grains, vegetables or animal meat, fat and by-products as a carrier composition with optional vitamins and minerals. The biscuit contains about 3-7 wt. % of an arthritis-treating combination, namely, glucosamine sulfate, vitamin C and an array of intracellular ions namely potassium, sodium and iodine. The glucosamine component is present by weight at approximately the same level as the vitamin C, and at approximately 10 (ten) times the level of the sum of the above-named intracellular ions. The biscuit is formulated so that its composition is approximately: Glucosamine component, 5 mg to 5,000 mg; Vitamin C component, 5 mg to 3,000 mg; Potassium component, 50 mcg to 150 mg; Sodium component, 50 mcg to 150 mg; and Iodine component, 25 mcg to 100 mg. The biscuit is dosed at approximately 10 mg glucosamine component per pound of body weight of the animal per day. This biscuit does not contain chondroitin sulfate, collagen or all the essential vitamins.

U.S. Pat. No. 6,596,303 to Bui et al. discloses pet food for maintenance of joint health and alleviation of arthritic symptoms in companion animals. The pet food comprises an effective amount of an active extract of *Perna canaliculus* (New Zealand Green Lipped Mussel). The extract can be either a powder or lipid extract. Preferably in an amount that provides for a dosage range of generally 0.18 to 114 mg of a powder extract/kg of body weight/day in a companion animal or an amount of generally 1.5 to 1000 mg of a powder extract of *Perna canaliculus* per 400 kcal of pet food product. This extract does not contain any vitamins.

U.S. Pat. No. 6,780,841 to Ishaq discloses hyaluronic acid and chondroitin sulfate based hydrolyzed collagen type II and a method of making same. This hydrolyzed collagen type II powder composition is used to induce cartilage formation and to treat connective tissue disorders by replenishing skin viscoelasticity. The compositions are administered through an orally ingestible delivery medium for absorption into the gastrointestinal tract. Chicken sternal cartilage-derived material is hydrolyzed to extract collagen type II by first cutting fresh chicken sternal cartilage to about 2 mm size, suspending the cartilage in an aqueous solution and treating the cartilage with a proteolytic enzyme such as papain, ficin and bromelain to form a hydrolysate having at least 20% of depolymerized chondroitin sulfate and at least 10% of hyaluronic acid. The hydrolyzed collagen type II has fragments having an average molecular weight of between about 5,500 to about 10,000 daltons and is sterilizied, concentrated and dried to form a powder.

U.S. Pat. No. 6,974,841 to Rapisarda discloses a pet antiaging wellness supplement. This health and nutrition supplement dosage for pets, particularly canine pets, consists essentially of anti-oxidant vitamins, B complex vitamins, bioflavonoids, chelated minerals, digestive enzymes, herbs, nutrients, and essential fatty acids amino acids and hormones. This supplement does not contain collagen, glucosamine or chondroitin sulfate.

Notwithstanding the efforts of prior art workers to provide a nutritional supplement to dogs and cats, there is a need for a supplement that meets the nutritional needs while at the same time protecting and/or rebuilding joint tissue. Since the tissue building process requires both collagen generating compositions as well as trace minerals and vitamins at the same time, taking these vitamin supplements and joint building supplements separately does not provide this joint building and/or protecting functionality. Also there is a need for maintaining the anti-oxidant level in the pet's blood stream to reduce degeneration of joint tissue by free radical associated damage.

SUMMARY OF THE INVENTION

The present invention provides a pet supplement formulation designed to provide vitamins and minerals, as well as formula components that protect and/or build joint tissue. The supplement may be administered as a paste, biscuit, jerky treat, chewable flavored tablet; or a sheet, chard or sliver adapted to dissolve on the tongue of an animal; or a powder appointed to be admixed with the animal's food. In each case, the supplement properly balances metabolic needs that match the joint building ingredients with vitamin and trace mineral content of the formulation. The joint building ingredient chicken collagen type II is selected to have a small molecular chain with a molecular weight in the range of 5,500 to 10,000. Another joint building ingredient, glucosamine sufate for example, needs a substantial quantity of ascorbic acid or vitamin C. However, the vitamin C of the composition is exhausted by the oxidation process of the glucosamine sulfate. More vitamin C is needed for the general upkeep of the pet. Trace copper is needed for cross-linking cartilage tissue and is provided in the mineral content in biologically usable form as chelates. The anti-oxidants provided prevent free radical damage, a key factor in preserving joints.

Generally stated, the pet supplement is provided in a single composition that is a completely mixed thereby each of the co-factors are made available to the pet's biological tissue at the same time allowing complete absorption of the nutritional formula. The formula comprises joint building components, vitamin components, mineral components, and anti-oxidant herbal components. The formulation is provided generally in the form of a biscuit or jerky treat or chewable tablet or other suitable form such as a chard, sheet or sliver adapted to dissolve on the tongue of an animal, or a powder adapted to be admixed with the animal's food; and contains a fixed quantity of these nutritional ingredients intimately mixed in a dry form. Providing proper dosage of this nutritional formulation to a pet based on its weight is extremely important. The biscuit or jerky treat is marked for a given weight size such as a 35 kilogram dog and is readily cut and proportioned according to the actual weight of the pet being treated. Likewise, the chard, sheet or sliver, as well as the powder, can be given in measured dosages depending on the animal's weight.

The formulation shown below is designed for an animal weighing 35 kilograms and has the following active ingredients.

| Joint preserving/building components | |
|---|---|
| Chicken collagen (as collagen type II) | 500-1800 mg |
| Glucosamine hydrochloride | 500-3500 mg |
| Chondroitin sulfate | 500-1500 mg |
| Vitamin components | |
| Vitamin C (as ascorbic acid) | 100-1500 mg |
| Vitamin D (as cholecalciforal) | 100-400 IU |
| Vitamin K (as phylloquinone) | 10-40 mcg |
| Mineral components | |
| Calcium (as calcium carbonate, calcium citrate, malate glycinate) | 400-600 mg |
| Magnesium (as Magnesium oxide magnesium glycinate) | 300-500 mg |
| Zinc (as zinc glycinate) | 10-20 mg |
| Copper (as copper glycinate) | 1-4 mg |
| Manganese (as manganese glycinate) | 3-8 mg |
| Boron (from Boron chelate) | 1-3 mg |
| Herbal cofactor blend | 300-1000 mg | comprising citrus bioflavonoids, red grapes anthocyanins (*vitis vinifera*) (skin), turmeric rhizome (*curcuma longa*), boswellia resin (*boswella serrata*) and fennel seed (*Foeniculum Vulgare*).

The formulation may contain inactive ingredients such as microcrystalline cellulose, croscamellose sodium, silica, magnesium stearate, pharmaceutical glaze and other ingredients that improve processability of the composition and the texture of the final product.

The preferred composition is set forth below.

| Joint preserving/building components | |
|---|---|
| Chicken collagen (as collagen type II) | 800 mg |
| Glucosamine hydrochloride | 1500 mg |
| Chondroitin sulfate | 1200 mg |
| Vitamin components | |
| Vitamin C (as ascorbic acid) | 100 mg |
| Vitamin D (as cholecalciforal) | 200 IU |
| Vitamin K (as phylloquinone) | 20 mcg |
| Mineral components | |
| Calcium (as calcium carbonate, calcium citrate, malate glycinate) | 500 mg |
| Magnesium (as Magnesium oxide magnesium glycinate) | 400 mg |
| Zinc (as zinc glycinate) | 15 mg |
| Copper (as copper glycinate) | 2 mg |
| Manganese (as manganese glycinate) | 5 mg |
| Boron (from Boron chelate) | 1.5 mg |
| Herbal cofactor blend | 500 mg |

Including citrus bioflavonoids, red grapes anthocyanins (*vitis vinifera*) (skin), turmeric rhizome (*curcuma longa*), boswellia resin (*boswella serrata*) and fennel seed (*Foeniculum Vulgare*).

The formulation may contain inactive ingredients such as microcrystalline cellulose, croscamellose sodium, silica, magnesium stearate, pharmaceutical glaze and other ingredients that improve processability of the composition and the texture of the final product.

The formulation has a pleasant flavor due to chicken products and is immediately consumed by pets. The formulation may also have additional flavor enhancers and taste enhancers for the pet.

DETAILED DESCRIPTION OF THE INVENTION

The present invention provides a pet formulation that provides the benefit of preserving or rebuilding joints of dogs and cats while at the same time synergistically providing vitamins and minerals, which are critically needed for building joint tissue and maintaining overall health. Antioxidants are provided in the form of a herbal co-factor blend in the formulation. The antioxidants reduce the activity of free radicals which, when present, contribute to joint degradation. The formulation is supplied as a ready to use paste, biscuit, jerky treat, chewable tablet; or a chard or sheet adapted to dissolve on the tongue of an animal; or a powder adapted to be admixed with the animal's food; which carries a fixed quantity of these joint preserving/joint rebuilding components, vitamin components, mineral components and an anti-oxidant, herbal co-factor blend for a fixed weight pet. Product containing the formulation is thereafter cut into segments, or administered in measured dosages, that are size and weight proportioned in accordance with the weight of the animal being treated.

Collagen occurs in many places throughout the body, and occurs in different forms known as types, which include: Type I collagen—This is the most abundant collagen of the body. It is present in scar tissue, the end product when tissue heals by repair. It is found in tendons and the organic part of bone. Type II collagen—Articular cartilage. Type III collagen—This is the collagen of granulation tissue, and is produced quickly by young fibroblasts before the tougher type I collagen is synthesized. Type IV collagen—basal lamina; eye lens Type V collagen—most interstitial tissue, assoc. with type I, associated with placenta Type VI collagen—most interstitial tissue, associated with type I. Type VII collagen—forms ancoring fibrils in dermal epidermal junctions. Type VIII collagen—some endothelial cells. Type IX collagen—FACIT collagen, cartilage, assoc. with type II and XI fibrils. Type X collagen—hypertrophic and mineralizing cartilage. Type XI collagen—cartilage. Type XII collagen—FACIT collagen, interacts with type I containing fibrils, decorin and glucosaminoglycans. Type XIII collagen—transmembrane collagen, interacts with integrin a1b1, fibronectin and components of basment membranes like nidogen and perlecan. As many as 28 types of collagen have previously been described in the literature.

One of the key elements of the composition of the subject invention is the inclusion of chicken collagen type II. Chicken collagen type II is extracted from the sternum (breast) bones of young chickens, which contain a large fraction of type II collagen. Type II collagen is the key type of collagen present in the joints. In addition, this extracted type II collagen also contains trace amounts of copper, which facilitates cross linking of collagen polymer chains to create high strength joints. As recently discussed by David E. Trentham, Roselynn A. Dynesius-Trentham, E. John Orav, Daniel Combitchi, Carlos Lorenzo, Kathryn Lea Sewell, David A. Hafler, and Howard L. Weiner in a paper entitled "Effects of Oral Administration of Type II Collagen on Rheumatoid Arthritis" published in journal of Science 261:1727-1729, 1993, it is clear that this chicken collagen of type II can be ingested orally and travel through the gastrointestinal tract without degradation. The mechanism of action exhibited by type II chicken collagen is believed to occur via oral tolerization to autoantigens. In addition, the digested type II chicken collagen also contains approximately 20% of depolymerized chondroitin sulfate and 10% of hyaluronic acid (HA) as indicated in U.S. Pat. No. 6,780,841. HA acts as a lubricant between connective tissues of the skin and protects the joints by providing shock-absorption. Decrease in HA levels is commonly associated with a great variety of disorders and ailments. For example, osteoarthritis patients experience decreased levels of HA in their synovial fluid. This has a detrimental effect on the joints because HA is primarily responsible for the lubricating and shock-absorbing effects of the synovial fluid. For this reason, researchers have theorized that the replacement of such lost HA may help osteoarthritis sufferers to rebuild damaged cartilage and to regain joint movement. Therefore, the key element of the invention is to add type II chicken collagen that can be orally ingested in combination with a well-balanced vitamin and mineral formulation with added antioxidants.

The length of the polymeric chain of the chicken collagen type II has a lot to do with its absorption in the animal's gastrointestinal tract. Smaller length chains are more easily absorbed. A digested chicken collagen type II with a molecular weight of 5,500 to 10,000 is ideally suited for the formulation since it absorbs at nearly the same rate as the vitamin, mineral and herbal co-factor blend of the supplement formulation.

Glucosamine is an amino sugar made of molecules called Glucosaminolglycans or "GAGS". GAGS are found in almost every tissue of the body including joints, tendons, ligaments, cartilage, skin and blood vessels. Glucosamine is needed to maintain normal joint fluid. Joint fluid surrounds the joints providing them with important nutrients. It helps to lubricate and cushion the joints, acting like a shock absorber during movement and insulating the bones from friction. Glucosamine is necessary to maintain the overall health and integrity of cartilage, bones and joints. It may also enhance the dog's mobility and flexibility.

Vitamin C is needed to regenerate and revitalize Vitamin E. It is also essential to normal collagen formation. Collagen is an integral part of the walls of the blood vessels and is part of the matrix of cartilage, tendons, ligaments, bones and skin.

Vitamin D plays an important role in the maintenance of an intact and strong skeleton. Its primary task is to regulate the amount of calcium and phosphorus in the blood by ensuring correct intake from intestines and secretion. Vitamin D3: cholecalciferol (made from 7-dehydrocholesterol), calcidiol, and calcitriol Calcium is essential for the normal growth and maintenance of bones and teeth. Calcium requirements must be met throughout the life of a pet. Long-term calcium deficiency can lead to osteoporosis, in which the bone deteriorates and there is an increased risk of fractures.

Magnesium ion is essential to the basic nucleic acid chemistry of life, and thus is essential to all cells of all known living organisms. Many enzymes require the presence of magnesium ions for their catalytic action, especially enzymes utilizing ATP, or those which use other nucleotides to synthesize DNA and RNA.

Zinc is an essential mineral and is a vital component of several biochemical and enzymatic reactions in a dog's body. In addition, zinc is needed to maintain the health and integrity of a dog's skin and hair coat.

Copper is essential in animals. Copper is carried mostly in the bloodstream on a plasma protein called ceruloplasmin. When copper is first absorbed in the gut it is transported to the liver bound to albumin. Copper is found in a variety of enzymes, including the copper centers of cytochrome c oxidase and the enzyme superoxide dismutase (containing copper and zinc). In addition to its enzymatic roles, copper is used for biological electron transport. The blue copper proteins that participate in electron transport include azurin and plastocyanin. The name "blue copper" comes from their intense blue color arising from a ligand-to-metal charge transfer (LMCT) absorption band around 600 nm. Copper is also essential in cross linking collagen.

Manganese is a trace mineral needed for vital enzyme reactions and proper bone development. It plays a key role in supporting the bodied production of vital elements required to rebuild cartilage in damaged joints.

Boron can drop excretion of calcium by 44%, and activate estrogen and vitamin D. This prevents bone loss.

Citrus bioflavonoids have been referred to as "nature's biological response modifiers" because of strong experimental evidence of their ability to modify the body's reaction to allergens, viruses, and carcinogens. They show anti-allergic, anti-inflammatory, anti-microbial and anti-cancer activity. In addition, flavonoids act as powerful antioxidants, protecting against oxidative and free radical damage.

Red grape anthocyanins are present together with other natural pigments like the closely chemically related flavonoids, carotenoids, anthoxanthins and betacyanins with similar anti-oxidant functionality.

Turmeric contains Curcumin has been used for thousands of years as a safe anti-inflammatory in a variety of ailments as part of Indian traditional medicine.

*Boswellia* is a genus of trees known for their fragrant resin, which has many pharmacological uses particularly as anti-inflamatories.

The preferred formulation is designed for an animal weighing 35 kilograms and has the following ingredients.

| Joint preserving/building components | |
|---|---|
| Chicken collagen (as collagen type II) | 800 mg |
| Glucosamine hydrochloride | 1500 mg |
| Chondroitin sulfate | 1200 mg |
| Vitamin components | |
| Vitamin C (as ascorbic acid) | 100 mg |
| Vitamin D (as cholecalciforal) | 200 IU |
| Vitamin K (as phylloquinone) | 20 mcg |
| Mineral components | |
| Calcium (as calcium carbonate, calcium citrate, malate glycinate) | 500 mg |
| Magnesium (as Magnesium oxide magnesium glycinate) | 400 mg |
| Zinc (as zinc glycinate) | 15 mg |
| Copper (as copper glycinate) | 2 mg |
| Manganese (as manganese glycinate) | 5 mg |
| Boron (from Boron chelate) | 1.5 mg |
| Herbal cofactor blend | 500 mg |

Including citrus bioflavonoids, red grapes anthocyanins (*vitis vinifera*) (skin), turmeric rhizome (*curcuma longa*), boswellia resin (*boswella serrata*) and fennel seed (*Foeniculum Vulgare*).

The formulation may contain inactive ingredients such as microcrystalline cellulose, croscamellose sodium, silica, magnesium stearate, pharmaceutical glaze and other ingredients that improve processability of the composition and the texture of the final product.

The formulation has a pleasant flavor due to chicken products and is immediately consumed by pets. The formulation may also have additional flavor enhancers and taste enhancers for the pet.

The key features of the joint preserving nutritional vitamin, mineral and herbal pet supplement include, in combination, the components set forth below:

1. a group of joint preserving/joint rebuilding compositions comprising chicken collagen type II, glucosamine hydrochloride and chondroitin sulfate incorporated within the pet supplement;
2. a group of vitamins comprising vitamin C, vitamin D and vitamin K incorporated within the pet supplement;
3. a group of minerals comprising calcium as calcium carbonate, calcium citrate, calcium malate or calcium glycinate, magnesium oxide or magnesium magnesium glycinate, zinc glycinate, copper glycinate, manganese glycinate and boron chelate incorporated within the pet supplement;
4. an anti-oxidant herb blend comprising citrus bioflavonoids, red grapes anthocyanins (*vitis vinifera*), turmeric rhizome (*curcuma longa*), boswellia resin (*boswella serrata*) and fennel seed (*Foeniculum Vulgare*) incorporated within the pet supplement;
5. the pet supplement having a dry mixed joint preserving/joint rebuilding composition, vitamin composition, mineral composition and herbal co-factor blend with a recipe designed for a certain weight of a pet and the supplement proportioned according to the weight of the pet being treated by the user;
6. the joint preservation/joint rebuilding process being optimized by synergic interaction of each of the compositions of the pet supplement delivered orally through the gastrointestinal tract of the animal simultaneously;
7. the pet supplement, delivered as a past, biscuit, jerky treat or chewable tablet; or as a sheet, chard or sliver adapted to dissolve on the tongue of an animal; or a powder appointed to be admixed with the animal's food, with pleasant chicken flavor, provides joint health and nutritional benefits to the pet through a single dose.

Having thus described the invention in rather full detail, it will be understood that such detail need not be strictly adhered to, but that additional changes and modifications may suggest themselves to one skilled in the art, all falling within the scope of the invention as defined by the subjoined claims.

What is claimed is:

1. A pet supplement comprising:
   a. a joint preserving/joint rebuilding composition comprising: 500-1800 mg type II chicken collagen; 500-3500 mg glucosamine hydrochloride; and 500-1500 mg chondroitin sulfate;
   b. a vitamin composition that works in conjunction with said joint preserving/joint rebuilding composition comprising 100-1500 mg vitamin C, 100-400 IU vitamin D and 10-40 mcg Vitamin K;
   c. a mineral composition comprising: 400-600 mg calcium as calcium carbonate, calcium citrate, calcium malate or calcium glycinate; 300-500 mg magnesium as magnesium oxide or magnesium glycinate; 10-20 mg zinc glycinate; 1-4 mg copper glycinate; 3-8 mg manganese glycinate; and 1-3 mg boron chelate;
   d. 300-1000 mg of a herbal cofactor blend comprising citrus bioflavonoids, red grapes anthocyanins, turmeric rhizome, boswellia resin and fennel seed;
   e. said type II chicken collagen is present in the range of in the range of 500mg to 1800 mg for a pet weighing 35 kilograms;
   f. said glucosamine hydrochloride is present in an amount ranging from 500mg to 3500 mg for a pet weighing 35 kilograms;
   g. said chondroitin sulfate is present in an amount ranging from 500 mg to 1500 mg for a pet weighing 35 kilograms;
   h. said vitamin C is present in an amount ranging from 100 mg to 1500 mg for a pet weighing 35 kilograms;
   i. said vitamin D is present in an amount ranging from 100 IU to 400 IU for a pet weighing 35 kilograms;
   j. said vitamin K is present in an amount ranging from 10 mcg to 40 mcg for a pet weighing 35 kilograms;
   k. said calcium is present in an amount ranging from 400 mg to 600 mg for a pet weighing 35 kilograms;
   l. said magnesium is present in an amount ranging from 300 mg to 500 mg for a pet weighing 35 kg;
   m. said zinc is present in an amount ranging from 10 mg to 20 mg for a pet weighing 35 kilograms;
   n. said copper is present in an amount ranging from 1 mg to 4 mg for a pet weighing 35 kilograms;
   o. said manganese is present in an amount ranging from 3 mg to 8 mg for a pet weighing 35 kilograms;
   whereby said components a-o are mixed in the supplement and orally delivered to the pet as segments proportioned according to pet weight to rebuild and preserve the pet's joint health.

2. A pet supplement as recited by claim 1, wherein said type II chicken collagen is present at a level of 800 mg for a pet weighing 35 kilograms.

3. A pet supplement as recited by claim 1, wherein said glucosamine hydrochloride is present at a level of 1500 mg for a pet weighing 35kilograms.

4. A pet supplement as recited by claim 1, wherein said chondroitin sulfate is present at a level of 1200 mg for a pet weighing 35 kilograms.

5. A pet supplement as recited by claim 1, wherein said vitamin C is present at a level of 100 mg for a pet weighing 35 kilograms.

6. A pet supplement as recited by claim 1, wherein said vitamin D is present at a level of 200 IU for a pet weighing 35 kilograms.

7. A pet supplement as recited by claim 1, wherein said vitamin K is present at a level of 20 mcg for a pet weighing 35 kilograms.

8. A pet supplement as recited by claim 1, wherein said calcium is present at a level of 500 mg for a pet weighing 35 kilograms.

9. A pet supplement as recited by claim 1, wherein said magnesium is present at a level of 400 mg for a pet weighing 35 kilograms.

10. A pet supplement as recited by claim 1, wherein said zinc is present at a level of 15 mg for a pet weighing 35 kilograms.

11. A pet supplement as recited by claim 1, wherein said copper is present at a level of 2 mg for a pet weighing 35 kilograms.

12. A pet supplement as recited by claim 1, wherein said manganese is present at a level of 5 mg for a pet weighing 35 kilograms.

13. A pet supplement as recited by claim 1, wherein said boron is present at a level of 1.5 mg for a pet weighing 35 kilograms.

14. A pet supplement as recited by claim 1, wherein said herbal cofactor blend is present at a level of 500 mg for a pet weighing 35 kilograms.

15. A pet supplement as recited by claim 1, in the form of a biscuit containing said joint preserving/joint rebuilding composition, said vitamin composition, said mineral composition and said herbal co-factor blend in an amount targeted for a specific weight of a pet.

16. A pet supplement as recited by claim 1 in the form of a jerky treat containing said joint preserving/joint rebuilding composition, said vitamin composition, said mineral composition and said herbal co-factor blend in an amount targeted for a specific weight of a pet.

17. A pet supplement as recited in claim 1 in the form of a chewable tablet containing said joint preserving/joint rebuilding composition, said vitamin composition, said mineral composition and said herbal co-factor blend in an amount targeted for a specific weight of a pet.

18. A pet supplement as recited in claim 1 in the form of a paste containing said joint preserving/joint rebuilding composition, said vitamin composition, said mineral composition and said herbal co-factor blend in an amount targeted for a specific weight of a pet.

19. A pet supplement as recited in claim 1 in the form of a sheet containing said joint preserving/joint rebuilding composition, said vitamin composition, said mineral composition and said herbal co-factor blend in an amount targeted for a specific weight of a pet.

20. A pet supplement as recited in claim 1 in the form of a chard containing said joint preserving/joint rebuilding composition, said vitamin composition, said mineral composition and said herbal co-factor blend in an amount targeted for a specific weight of a pet.

21. A pet supplement as recited in claim 1 in the form of a sliver containing said joint preserving/joint rebuilding composition, said vitamin composition, said mineral composition and said herbal co-factor blend in an amount targeted for a specific weight of a pet.

22. A pet supplement as recited in claim 1 in the form of a powder containing said joint preserving/joint rebuilding composition, said vitamin composition, said mineral composition and said herbal co-factor blend in an amount targeted for a specific weight of a pet.

23. A pet supplement comprising:
   a. a joint preserving/joint rebuilding composition comprising: 800 mg type II chicken collagen; 1500 mg glucosamine hydrochloride; and 1200 mg chondroitin sulfate;
   b. a vitamin composition that works in conjunction with said joint preserving/joint rebuilding composition comprising 100 mg vitamin C, 200 IU vitamin D and 20 mcg Vitamin K;
   c. a mineral composition comprising: 500 mg calcium as calcium carbonate, calcium citrate, calcium malate or calcium glycinate; 400 mg magnesium as magnesium oxide or magnesium glycinate; 15 mg zinc glycinate; 2 mg copper glycinate; 5 mg manganese glycinate; and 1.5 mg boron chelate;
   d. 500 mg of a herbal cofactor blend comprising citrus bioflavonoids, red grapes anthocyanins, turmeric rhizome, boswellia resin and fennal seed;
   e. said type II chicken collagen is present in an amount of 800 mg for a pet weighing 35 kilograms;
   f. said glucosamine hydrochloride is present in an amount of 1500 mg for a pet weighing 35 kilograms;
   g. said chondroitin sulfate is present in an amount of 1200 mg for a pet weighing 35 kilograms;
   h. said vitamin C is present in an amount of 100 mg for a pet weighing 35 kilograms;
   i. said vitamin D is present in an amount of 200 IU for a pet weighing 35 kilograms;
   j. said vitamin K is present in an amount of 20 mcg for a pet weighing 35 kilograms;
   k. said calcium is present in an amount of 500 mg for a pet weighing 35 kilograms;
   l. said magnesium is present in an amount of 400 mg for a pet weighing 35 kg;
   m. said zinc is present in an amount of 15 mg for a pet weighing 35 kilograms;
   n. said copper is present in an amount of 2 mg for a pet weighing 35 kilograms;
   o. said manganese is present in an amount of 5 mg for a pet weighing 35 kilograms;
   whereby said components a-o are mixed in the supplement and orally delivered to the pet as segments proportioned according to pet weight to rebuild and preserve the pet's joint health.

* * * * *